US008575081B2

(12) United States Patent
Miller et al.

(10) Patent No.: US 8,575,081 B2
(45) Date of Patent: *Nov. 5, 2013

(54) SYNTHESIS OF DIESTER-BASED BIOLUBRICANTS FROM EPOXIDES

(75) Inventors: Stephen Joseph Miller, San Francisco, CA (US); Zhen Zhou, Emeryville, CA (US); Saleh A. Elomari, Fairfield, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 250 days.

This patent is subject to a terminal disclaimer.

(21) Appl. No.: 12/962,193

(22) Filed: Dec. 7, 2010

(65) Prior Publication Data

US 2011/0077184 A1 Mar. 31, 2011

Related U.S. Application Data

(63) Continuation of application No. 12/023,695, filed on Jan. 31, 2008, now Pat. No. 7,867,959.

(51) Int. Cl.
*C07C 67/00* (2006.01)

(52) U.S. Cl.
USPC .......................................................... 508/465

(58) Field of Classification Search
USPC .......................................................... 508/465
See application file for complete search history.

(56) References Cited

U.S. PATENT DOCUMENTS

| 2,025,684 | A |  | 12/1935 | Hansley et al. |
| 2,537,283 | A |  | 1/1951 | Schaad |
| 3,211,801 | A |  | 10/1965 | Holm et al. |
| 3,270,085 | A |  | 8/1966 | Noddings et al. |
| 3,304,343 | A |  | 2/1967 | Mitsutani |
| 3,327,014 | A |  | 6/1967 | Noddings |
| 3,393,225 | A |  | 7/1968 | Fenton |
| 3,448,164 | A |  | 6/1969 | Holm et al. |
| 3,723,564 | A |  | 3/1973 | Tidwell et al. |
| 4,593,146 | A |  | 6/1986 | Johnson et al. |
| 4,943,383 | A | * | 7/1990 | Avery et al. .................. 508/304 |

(Continued)

FOREIGN PATENT DOCUMENTS

GB 1231185 5/1971
JP 54132517 10/1979

OTHER PUBLICATIONS

Kim, Jong Dae et al., Synthesis of 4,5-bis(hexanoyloxy) and the Lubricity, Database CA [Online]; Chemical Abstracts Service, Columbus, Ohio, US;, retrieved from STN, Database accession No. 1987:69869; & Kicho Kwahak Yongu (Yeungnam Taehakkyo) , 5, 129-35 Coden: KKWYDR, 1985.
PCT/US08/83899 International Search Report.

(Continued)

*Primary Examiner* — Taiwo Oladapo
(74) *Attorney, Agent, or Firm* — Jeffrey M. McQuiston; Ted Mickelson

(57) ABSTRACT

The present invention is generally directed to methods of making diester-based lubricant compositions, wherein formation of diester species proceeds via direct esterification of epoxide intermediates. In some embodiments, the methods for making such diester-based lubricants utilize a biomass precursor and/or low value (e.g., Fischer-Tropsch (FT) olefins and/or alcohols) so as to produce high value diester-based lubricants. In some embodiments, such diester-based lubricants are derived from FT olefins and fatty acids. The fatty acids can be from a bio-based source (i.e., biomass, renewable source) or can be derived from FT alcohols via oxidation.

14 Claims, 6 Drawing Sheets

Step 101 - epoxidizing an olefin to form an epoxide comprising an epoxide ring.

Step 102 - directly esterifying the epoxide with a carboxylic acid to form a diester species.

(56) References Cited

U.S. PATENT DOCUMENTS

| | | |
|---|---|---|
| 5,047,159 A | 9/1991 | Zehler |
| 5,141,663 A * | 8/1992 | Miller ............................ 252/79 |
| 5,733,860 A | 3/1998 | Durbut et al. |
| 6,150,458 A | 11/2000 | Weikard et al. |
| 6,281,404 B1 | 8/2001 | Miller |
| 6,290,869 B1 | 9/2001 | Sorensen et al. |
| 7,867,959 B2 | 1/2011 | Miller et al. |
| 8,097,740 B2 * | 1/2012 | Miller .......................... 554/148 |
| 2002/0072479 A1* | 6/2002 | Williamson et al. .......... 508/459 |
| 2003/0199717 A1 | 10/2003 | Miller |
| 2006/0019840 A1 | 1/2006 | Kawahara et al. |
| 2007/0203358 A1 | 8/2007 | Dirkzwager et al. |
| 2008/0194444 A1 | 8/2008 | Miller et al. |
| 2008/0248982 A1* | 10/2008 | Miller et al. .................. 508/485 |

OTHER PUBLICATIONS

PCT/US2008/83899 International Search Report mailed Jan. 9, 2009.

* cited by examiner

Scheme 1

Scheme 2

Hexanoic acid 2-hexanoyloxy-1-hexyl-octyl ester (9)

Decanoic acid 2-decanoyloxy-1-hexyl-octyl ester (10)

SYNTHESIS OF DIESTER-BASED BIOLUBRICANTS FROM EPOXIDES

CROSS-REFERENCE TO RELATED APPLICATIONS

This application for patent is a Continuation of U.S. patent application Ser. No. 12/023,695; filed Jan. 31, 2008.

FIELD OF THE INVENTION

This invention relates to methods of making ester-based lubricants, and specifically to methods of synthesizing diester-based lubricants—particularly wherein they are made from at least one biologically-derived precursor.

BACKGROUND

Esters have been used as lubricating oils for over 50 years. They are used in a variety of applications ranging from jet engines to refrigeration. In fact, esters were the first synthetic crankcase motor oils in automotive applications. However, esters gave way to polyalphaolefins (PAOs) due to the lower cost of PAOs and their formulation similarities to mineral oils. In fully synthetic motor oils, however, esters are almost always used in combination with PAOs to balance the effect on seals, additive solubility, volatility reduction, and energy efficiency improvement by enhanced lubricity.

Ester-based lubricants, in general, have excellent lubrication properties due to the polarity of the ester molecules of which they are comprised. The polar ester groups of such molecules adhere to positively-charged metal surfaces creating protective films which slow down the wear and tear of the metal surfaces. Such lubricants are less volatile than the traditional lubricants and tend to have much higher flash points and much lower vapor pressures. Ester lubricants are excellent solvents and dispersants, and can readily solvate and disperse the degradation by-products of oils. Therefore, they greatly reduce sludge buildup. While ester lubricants are stable to thermal and oxidative processes, the ester functionalities give microbes a handle with which to do their biodegrading more efficiently and more effectively than their mineral oil-based analogues—thereby rendering them more environmentally-friendly. However, the preparation of esters is more involved and more costly than the preparation of their PAO counterparts.

Recently, novel diester-based lubricant compositions and their corresponding syntheses have been described in commonly-assigned U.S. patent application Ser. No. 11/673,879; filed Feb. 12, 2007. The synthetic routes described in this patent application comprise and/or generally proceed through the following sequence of reaction steps: (1) epoxidation of an olefin to form an epoxide; (2) conversion of the epoxide to form a diol; and (3) esterification of the diol to form a diester.

In view of the foregoing, and not withstanding such above-described advances in diester-based lubricant synthesis, a simpler, more efficient method of generating ester-based would be extremely useful—particularly wherein such methods utilize renewable raw materials in possible combination with the conversion of low value precursors (e.g., Fischer-Tropsch olefins and/or alcohols) to high value ester lubricants.

BRIEF DESCRIPTION OF THE INVENTION

The present invention is generally directed to methods of making diester-based lubricant compositions. In some embodiments, the methods for making such diester-based lubricants utilize a biomass precursor. In these or other embodiments, lubricant precursor species can also be sourced or otherwise derived from Fischer-Tropsch (FT) reaction products and/or the pyrolysis of waste plastic.

In some embodiments, the present invention is directed to processes comprising the steps of (a) epoxidizing an olefin having a carbon number of from R to 16 to form an epoxide comprising an epoxide ring; and (b) directly esterifying the epoxide with a $C_2$ to $C_{18}$ carboxylic acid to form a diester species having viscosity and pour point suitable for use as a lubricant. Such direct esterification generally proceeds without the production and isolation of a diol intermediate that is subsequently esterified. Additionally, such epoxidizing and direct esterifying are typically carried out on a plurality of olefins and epoxides, respectively.

Typically, the lubricant compositions produced by the above-mentioned process comprise a quantity of at least one diester species, the diester species having the following structure:

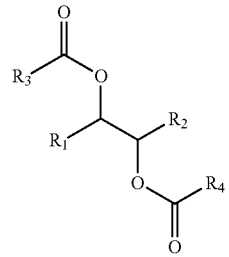

wherein $R_1$, $R_2$, $R_3$, and $R_4$ are the same or independently selected from $C_2$ to $C_{17}$ hydrocarbon groups.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

1. Introduction

Figure 1:
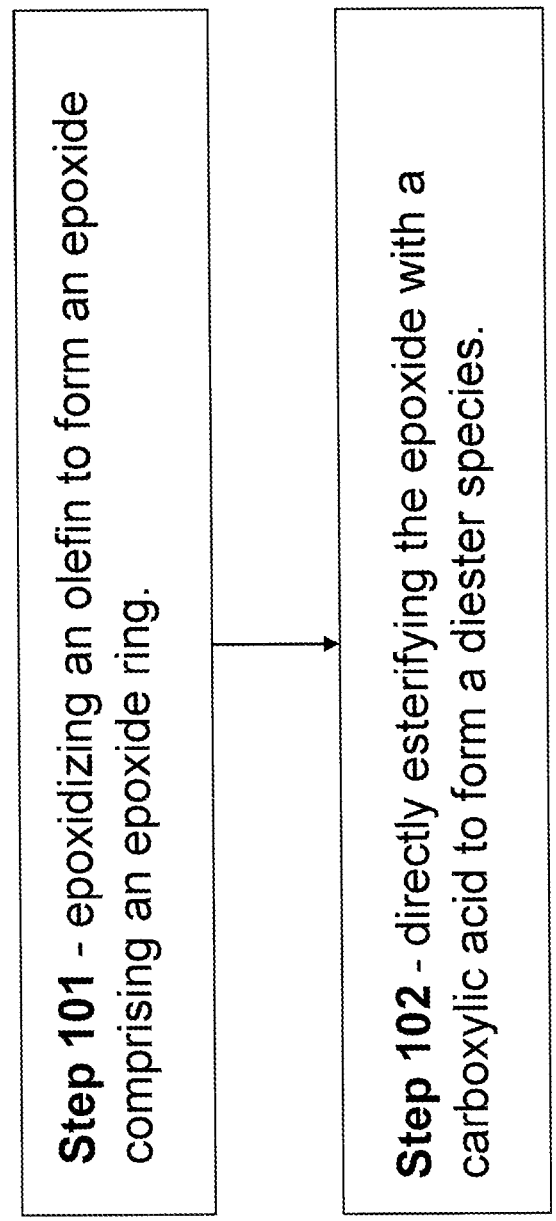
FIG. 1 is a flow diagram illustrating a method of making diester-based lubricant compositions, wherein the associated synthesis comprises a direct esterification of an epoxide intermediate—in accordance with some embodiments of the present invention.

As mentioned in a preceding section, the present invention is directed to methods of making diester-based lubricant compositions. In some embodiments, such methods for making such diester-based lubricants utilize a biomass precursor and/or low value olefins and/or alcohols (e.g., those derived from Fischer-Tropsch (FT) processes) so as to produce high value diester-based lubricants. In some embodiments, such diester-based lubricants are derived from FT olefins and fatty (carboxylic) acids. In these or other embodiments, the fatty acids can be from a bio-based source (i.e., biomass, renewable source) and/or can be derived from FT alcohols via oxidation.

Because biolubricants and biofuels are increasingly capturing the public's attention and becoming topics of focus for many in the oil industry, the use of biomass in the making of such above-mentioned lubricants could be attractive from several different perspectives. To the extent that biomass is so utilized in the making of the diester-based lubricants of the present invention, such lubricants are deemed to be biolubricants.

2. Definitions

"Lubricants," as defined herein, are substances (usually a fluid under operating conditions) introduced between two moving surfaces so to reduce the friction and wear between them. Base oils used as motor oils are generally classified by the American Petroleum Institute as being mineral oils (Group I, II, and III) or synthetic oils (Group IV and V). See American Petroleum Institute (API) Publication Number 1509.

"Pour point," as defined herein, represents the lowest temperature at which a fluid will pour or flow. See, e.g., ASTM International Standard Test Methods D 5950-96, D 6892-03, and D 97.

"Cloud point," as defined herein, represents the temperature at which a fluid begins to phase separate due to crystal formation. See, e.g., ASTM Standard Test Methods D 5773-95, D 2500, D 5551, and D 5771.

"Centistoke," abbreviated "cSt," is a unit for kinematic viscosity of a fluid (e.g., a lubricant), wherein 1 centistoke equals 1 millimeter squared per second (1 cSt=1 mm$^2$/s). See, e.g., ASTM Standard Guide and Test Methods D 2270-04, D 445-06, D 6074, and D 2983.

With respect to describing molecules and/or molecular fragments herein, "Rn," where "n" is an index, refers to a hydrocarbon group, wherein the molecules and/or molecular fragments can be linear and/or branched.

As defined herein, "$C_n$," where "n" is an integer, describes a hydrocarbon molecule or fragment (e.g., an alkyl group) wherein "n" denotes the number of carbon atoms in the fragment or molecule.

The prefix "bio," as used herein, refers to an association with a renewable resource of biological origin, such resources generally being exclusive of fossil fuels.

The term "internal olefin," as used herein, refers to an olefin (i.e., an alkene) having a non-terminal carbon-carbon double bond (C=C). This is in contrast to "α-olefins" which do bear a terminal carbon-carbon double bond.

3. Diester Lubricant Compositions

Methods of the present invention generally provide for diester-based lubricant compositions comprising a quantity of (vicinal) diester species having the following chemical structure:

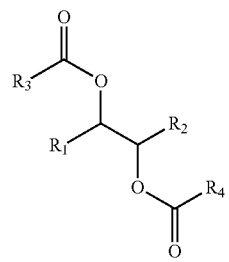

where $R_1$, $R_2$, $R_3$, and $R_4$ are the same or independently selected from a $C_2$ to $C_{17}$ carbon fragment.

Regarding the above-mentioned diester species, selection of $R_1$, $R_2$, $R_3$, and $R_4$ can follow any or all of several criteria. For example, in some embodiments, $R_1$, $R_2$, $R_3$, and $R_4$ are selected such that the kinematic viscosity of the composition at a temperature of 100° C. is typically 3 centistokes (cSt) or greater. In some or other embodiments, $R_1$, $R_2$, $R_3$, and $R_4$ are selected such that the pour point of the resulting lubricant is −20° C. or lower. In some embodiments, $R_1$ and $R_2$ are selected to have a combined carbon number (i.e., total number of carbon atoms) of from 6 to 14. In these or other embodiments, $R_3$ and $R_4$ are selected to have a combined carbon number of from 10 to 34. Depending on the embodiment, such resulting diester species can have a molecular mass between 340 atomic mass units (a.m.u.) and 780 a.m.u.

In some embodiments, such above-described compositions are substantially homogeneous in terms of their diester component. In some or other embodiments, the diester component of such compositions comprises a variety (i.e., a mixture) of diester species. In some embodiments, the diester-based lubricant composition that is produced comprises at least one diester species derived from a $C_8$ to $C_{14}$ olefin and a $C_6$ to $C_{14}$ carboxylic acid.

In some of the above-described embodiments, the diester-based lubricant composition comprises diester species selected from the group consisting of decanoic acid 2-decanoyloxy-1-hexyl-octyl ester and its isomers, tetradecanoic acid-1-hexyl-2-tetradecanoyloxy-octyl esters and its isomers, dodecanoic acid 2-dodecanoyloxy-1-hexyl-octyl ester and its isomers, hexanoic acid 2-hexanoyloxy-1-hexy-octyl ester and its isomers, octanoic acid 2-octanoyloxy-1-hexyl-octyl ester and its isomers, _hexanoic acid 2-hexanoyloxy-1-pentyl-heptyl ester and isomers, octanoic acid 2-octanoyloxy-1-pentyl-heptyl ester and isomers, decanoic acid 2-decanoyloxy-1-pentyl-heptyl ester and isomers, decanoic acid-2-cecanoyloxy-1-pentyl-heptyl ester and its isomers, dodecanoic acid-2-dodecanoyloxy-1-pentyl-heptyl ester and isomers, tetradecanoic acid 1-pentyl-2-tetradecanoyloxy-heptyl ester and isomers, tetradecanoic acid 1-butyl-2-tetradecanoyloxy-hexyl ester and isomers, dodecanoic acid-1-butyl-2-dodecanoyloxy-hexyl ester and isomers, decanoic acid 1-butyl-2-decanoyloxy-hexyl ester and isomers, octanoic acid 1-butyl-2-octanoyloxy-hexyl ester and isomers, hexanoic acid 1-butyl-2-hexanoyloxy-hexyl ester and isomers, tetradecanoic acid 1-propyl-2-tetradecanoyloxy-pentyl ester and isomers, dodecanoic acid 2-dodecanoyloxy-1-propyl-pentyl ester and isomers, decanoic acid 2-decanoyloxy- 1-propyl-pentyl ester and isomers, octanoic acid 2-octanoyloxy-1-propyl-pentyl ester and isomers, hexanoic acid 2-hexanoyloxy-1-propyl-pentyl ester and isomers, and mixtures thereof.

It is worth noting that, in most applications, the above-described esters and their compositions are unlikely to be used as lubricants by themselves, but are usually used as blending stocks. As such, esters with higher pour points may also be used as blending stocks with other lubricant oils since they are very soluble in hydrocarbons and hydrocarbon-based oils.

4. Methods of Making Diester Lubricants

As mentioned above, the present invention is generally directed to methods of making the above-described lubricant compositions.

Referring to the flow diagram shown in FIG. 1, in some embodiments processes for making the above-mentioned (vicinal) diester species, typically having lubricating base oil viscosity and pour point, comprise the following steps: (Step 101) epoxidizing an olefin (or quantity of olefins) having a carbon number of from 8 to 16 to form an epoxide comprising an epoxide ring; and (Step 102) directly esterifying (subjecting to esterification, i.e., diacylating) the epoxide with an $C_2$ to $C_{18}$ carboxylic acid to form a diester species. Generally, lubricant compositions comprising such diester species have a viscosity of 3 centistokes or more at a temperature of 100° C. It will be appreciated by those of skill in the art that, in the steps of epoxidizing and esterifying, a plurality of olefins and epoxides, respectively, are typically so reacted, so as to effect the production of a plurality of diester species.

In some embodiments, where a quantity of such diester species is formed, the quantity of diester species can be substantially homogeneous, or it can comprise a mixture of two or more different such diester species.

In some embodiments, the diester so formed is mixed or admixed with a base oil selected from the group consisting of Group I oils, Group II oils, Group III oils, and mixtures thereof.

In some such above-described method embodiments, the olefin used is a reaction product of a Fischer-Tropsch process. In some or other embodiments, the olefin used is derived from the pyrolysis of waste plastic. Generally speaking, however, the source of the olefin(s) is not particularly limited.

In some embodiments, the olefin is an α-olefin (i.e., an olefin having a double bond at a chain terminus). In such embodiments, it is often necessary to isomerize the olefin so as to internalize the double bond. Such isomerization is typically carried out catalytically using a catalyst such as, but not limited to, crystalline aluminosilicate and like materials and aluminophosphates. See, e.g., U.S. Pat. Nos. 2,537,283; 3,211,801; 3,270,085; 3,327,014; 3,304,343; 3,448,164; 4,593,146; 3,723,564 and 6,281,404; the last of which claims a crystalline aluminophosphate-based catalyst with 1-dimensional pores of size between 3.8 Å and 5 Å.

Figure 2:
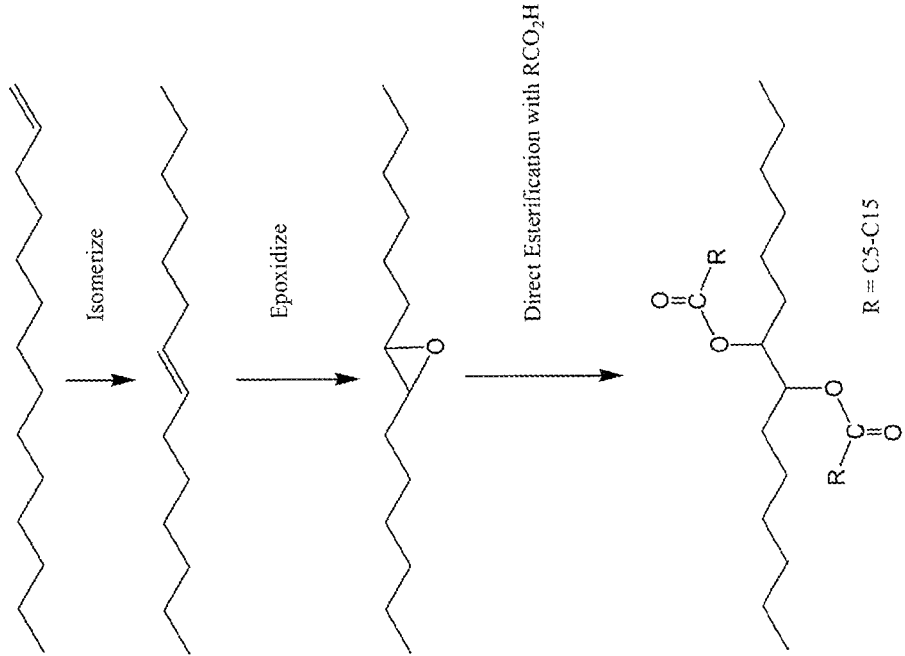
FIG. 2 (Scheme 1) is a chemical flow diagram illustrating an exemplary method of making a diester-based lubricant composition without the production and isolation of a diol intermediate, in accordance with some embodiments of the present invention.

As an example of such above-described isomerizing and as indicated in Scheme 1 (FIG. 2), Fischer-Tropsch alpha olefins (α-olefins) can be isomerized to the corresponding internal olefins followed by epoxidation. The epoxides can then be transformed to the corresponding diesters via direct (di)-esterification with the appropriate carboxylic acids. It is typically necessary to convert alpha olefins to internal olefins because diesters of alpha olefins, especially short chain alpha olefins, tend to be solids or waxes. "Internalizing" alpha olefins followed by transformation to the diester functionalities introduces branching along the chain which reduces the pour point of the intended products. The ester groups with their polar character would further enhance the viscosity of the final product. Adding branches during the isomerizing (isomerization) step will tend to increase carbon number and hence viscosity. It can also decrease the associated pour and cloud points. It is typically preferable to have a few longer branches than many short branches, since increased branching tends to lower the viscosity index (VI)

Regarding the step of epoxidizing (i.e., the epoxidation step), in some embodiments, the above-described olefin (preferably an internal olefin) can be reacted with a peroxide (e.g., $H_2O_2$) or a peroxy acid (e.g., peroxyacetic acid) to generate an epoxide. See, e.g., D. Swern, in *Organic Peroxides Vol. II*, Wiley-Interscience, New York, 1971, pp. 355-533; and B. Plesnicar, in Oxidation in *Organic Chemistry, Part C*, W. Trahanovsky (ed.), Academic Press, New York 1978, pp. 221-253.

Regarding the step of directly esterifying (i.e., the esterification step), in some embodiments this step is carried out in the presence of a catalyst. Such catalyst species can include, but are not limited to, $H_3PO_4$, $H_2SO_4$, sulfonic acid, Lewis acids, silica and alumina-based solid acids, amberlyst, tungsten oxide, and mixtures and combinations thereof, and the like.

In some such above-described method embodiments, the carboxylic acid can be derived from alcohols generated by a Fischer-Tropsch process and/or it can be a bio-derived fatty acid. Note that the carboxylic acids can be of a single type (e.g., length), or they can be a mixture of types. Additionally, in some embodiments, quantities of carboxylic acid anhydride can also be utilized together with the carboxylic acid in the esterification.

In some embodiments, during the step of directly esterifying, efforts are made to remove water produced as a result of the esterifying process. Such efforts can positively impact the diester yield.

Regardless of the source of the olefin, in some embodiments, the carboxylic acid used in the above-described method is derived from biomass. In some such embodiments, this involves the extraction of some oil (e.g., triglyceride) component from the biomass and hydrolysis of the triglycerides of which the oil component is comprised so as to form free carboxylic acids.

5. Variations

Variations (i.e., alternate embodiments) on the above-described lubricant compositions include, but are not limited to, utilizing mixtures of isomeric olefins and or mixtures of olefins having a different number of carbons. This leads to diester mixtures in the product compositions. Variations on the above-described processes further include, but are not limited to, using carboxylic acids derived from FT alcohols by oxidation.

The advantages of the methods of the present invention notwithstanding, in some embodiments, it may be advantageous to combine the methods of the present invention with those described in commonly-assigned U.S. patent application Ser. No. 11/673,879, filed Feb. 12, 2007 and incorporated by reference herein.

6. Examples

The following examples are provided to demonstrate, and/or more fully illustrate, particular embodiments of the present invention. It should be appreciated by those of skill in the art that the methods disclosed in the examples which follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

Example 1

This Example serves to illustrate the epoxidation of tetradecenes to form tetradecene epoxides, and the subsequent esterification of the tetradecene epoxides to form diester species operable for use in/as diester-based lubricant compositions, in accordance with some embodiments of the present invention.

Tetradecenes were epoxidized as follows using a general procedure for the epoxidation of 7,8-tetradecene. To a stirred solution of 143 grams (0.64 mole) of 77% mCPBA (meta-chloroperoxybenzoic acid) in 500 mL chloroform, 100 grams (0.51 mol) of 7,8-tetradecene in 200 mL chloroform was added drop-wise over a 45-minute period. The resulting reaction mixture was stirred overnight. The resulting milky solution was subsequently filtered to remove meta-chloro-benzoic acid that formed therein. The filtrate was then washed with a 10% aqueous solution of sodium bicarbonate. The organic layer was dried over anhydrous magnesium sulfate and concentrated on a rotary evaporator. The reaction afforded the desired epoxide (isomers of n-tetradecene epoxides) as colorless oil in 93% yield.

Figure 3:
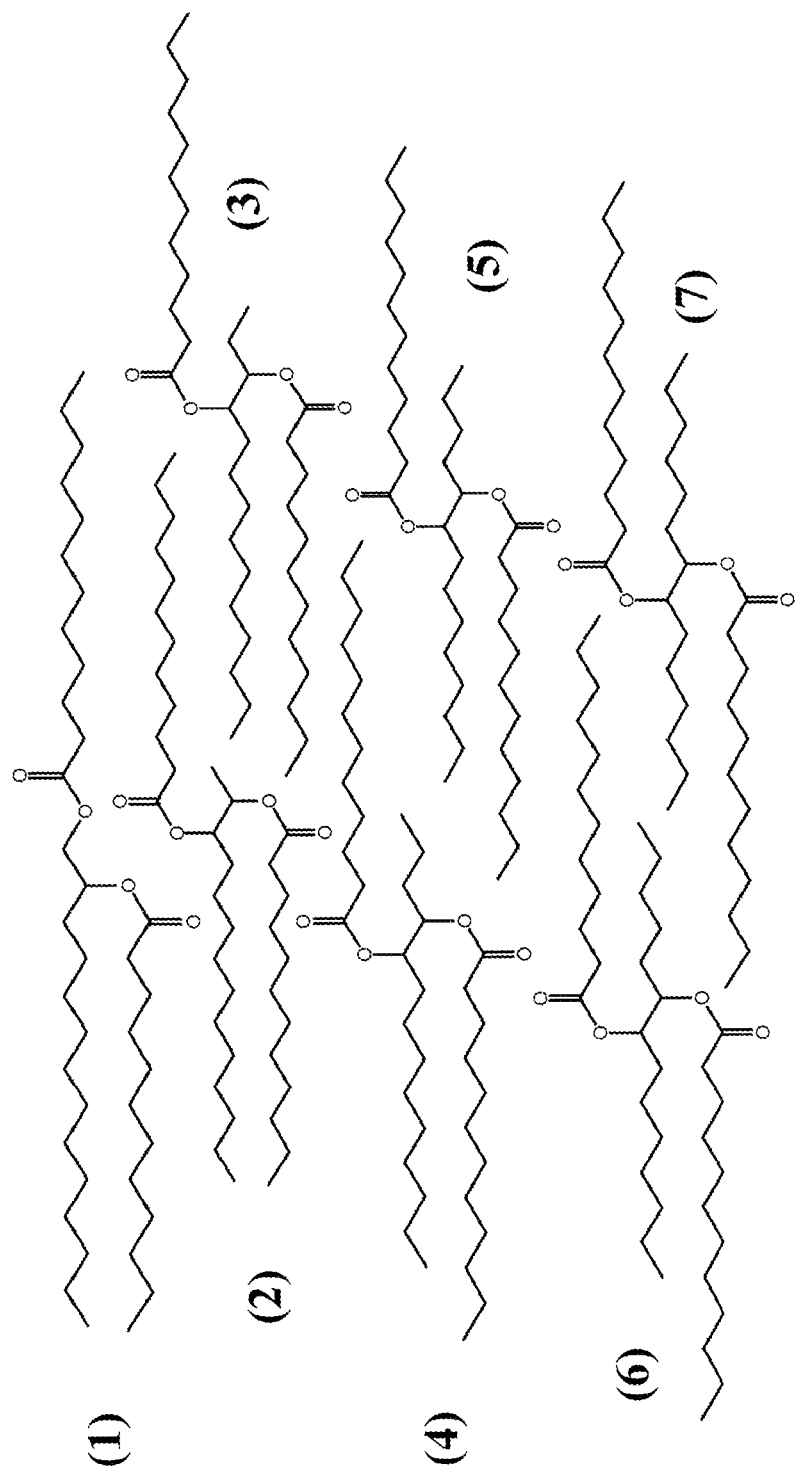
FIG. 3 depicts an exemplary mixture of species 1-7 that can be produced via methods of the present invention.

The isomers of n-tetradecene epoxides (10.6 grams, 50 mmol) were mixed with lauric acid (30 grams, 150 mmol) and 85% $H_3PO_4$ (0.1 grams, 0.87 mmol). The mixture was stirred and bubbled/purged with nitrogen at 150° C. for 20 hours. Excess lauric acid was removed from the product first by recrystallization in hexane with subsequent filtration at −15° C., and then by adding a calculated amount of 1N NaOH solution and filtering out the sodium laurate salt. The diester product collected (21.8 grams, 73% yield) was a light yellow, transparent oil. The oil comprised a mixture of the diester species 1-7 depicted in FIG. 3.

Example 2

This Example serves to illustrate the direct esterification of 1-dodecene epoxide (2-decyl-oxirane) to yield a diester species, in accordance with some embodiments of the present invention.

Figure 4:
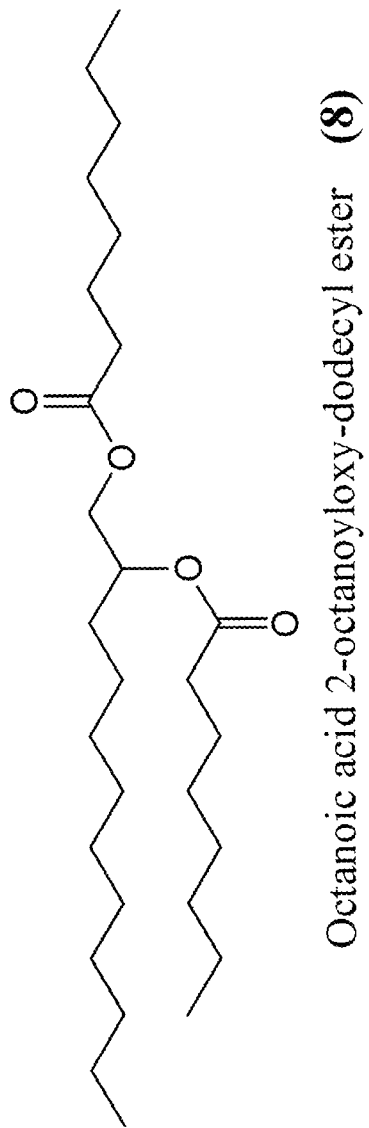
FIG. 4 depicts an exemplary species 8, octanoic acid 2-octanoyloxy-dodecyl ester, that can be produced via methods of the present invention.

Quantities of 1-dodecene epoxide (9.2 grams, 50 mmol) and octanoic acid (14.4 grams, 100 mmol) were dissolved in 12 mL toluene, and 85% $H_3PO_4$ (0.3 grams, 0.87 mmol) was added. The mixture was stirred and bubbled/purged with nitrogen at 140° C. for 23 hours. The mixture was subsequently washed with a $K_2CO_3$-saturated solution, filtered and separated to remove the acids, the organic layer was dried by anhydrous $MgSO_4$ and evaporated under reduced pressure. Referring to FIG. 4, the diester product 8, octanoic acid 2-octanoyloxy-dodecyl ester, (18 grams, 83% yield) was a transparent, colorless oil.

Example 3 (Comparative)

Figure 5:
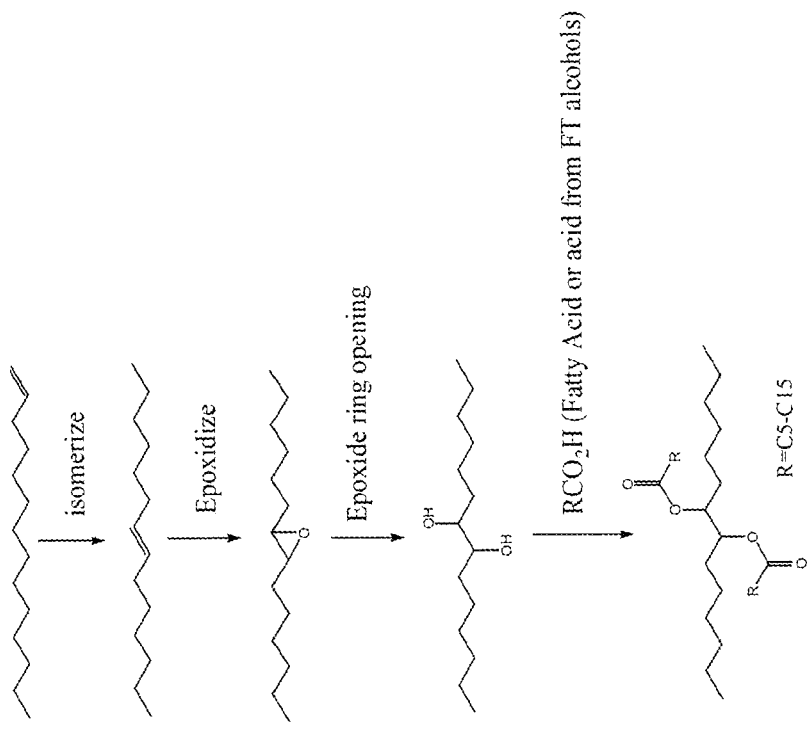
FIG. 5 (Scheme 2); is a chemical flow diagram illustrating a previously-presented (prior art) method for generating diester species operable for use in lubricant compositions and is shown primarily for comparative purposes.

This Example serves to illustrate synthesis and isolation of a diol, and subsequent esterification of said diol, en route to synthesis of a diester species, in accordance with the methods described in commonly-assigned U.S. patent application Ser. No. 11/673,879, filed Feb. 12, 2007 and incorporated by reference herein. This comparative Example differs from embodiments of the present invention in that a diol is produced and isolated for subsequent esterification (as depicted in FIG. 5, Scheme 2), instead of esterifying the epoxide directly.

1. Diol Preparation and Isolation

In a 3-neck 1 mL reaction flask equipped with an overhead stirrer and an ice bath, 75 mL of 30% hydrogen peroxide were added to 300 mL of 96% formic acid. To this mixture, 100 grams (0.51 mole) of 7-tetradecene (purchased from Aldrich Chemical Co.) was added slowly over a 30 minute period via a dropping funnel. Once the addition of the olefin was complete, the reaction was allowed to stir while cooling with the ice-bath to prevent rise in the temperature above 40-50° C. for 2 hrs. The ice-bath was then removed and the reaction was stirred at room temperature overnight. The reaction mixture was concentrated with a rotary evaporator in a hot water bath at ~30 torr to remove most of the water and formic acid. Then, 100 mL of ice-cold 1 M solution of sodium hydroxide was added very slowly (in small portions) and carefully to the remaining residue of the reaction. Once all the sodium hydroxide solution was added, the mixture was allowed to stir for an additional 45-60 minutes at room temperature. The mixture was diluted with 500 mL ethyl acetate and transferred to a reparatory funnel. The organic layer was sequestered and the aqueous layer was extracted 3 times (3×200 mL) with ethyl acetate. The ethyl acetate extracts were combined and dried over anhydrous $MgSO_4$. Filtration, followed by concentration on a rotary evaporator at reduced pressure in a hot water bath gave the desired diol as white powder in 88% yield (95 grams). The produced and isolated diol (tetradecane-7,8-diol) was characterized by nuclear magnetic resonance (NMR) spectroscopy and gas-chromatography/mass spectrometry (GC/MS).

2. Conversion of the Diol to a Diester

Figure 6:
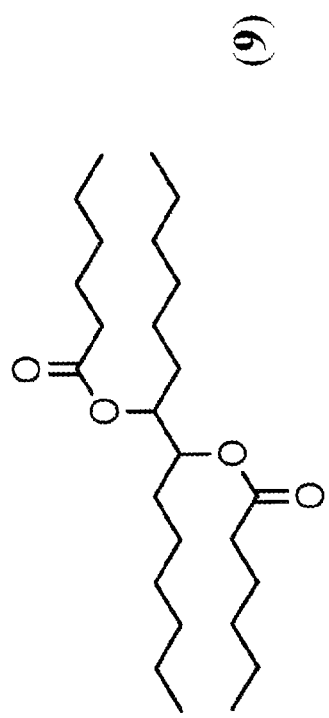
FIG. 6 depicts two diester-based compounds 9 and 10, prepared via methods described previously and presented here primarily for comparative purposes.
Figure 6:
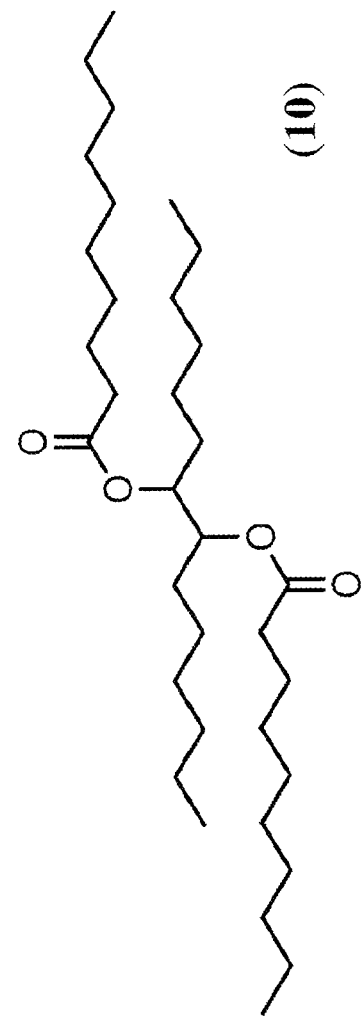

What follows serves to illustrate synthesis of diester 10 (decanoic acid 2-decanoyloxy-1-hexyl-octyl ester) from tetradecane-7,8-diol (see above). FIG. 6 depicts diester 10, as well as diester 9 (hexanoic acid 2-hexanoyloxy-1-hexyl-octyl ester), the latter being similarly prepared by using hexanoic acid or an anhydrous variant thereof.

In a 3-neck 1 L reaction flask equipped with an overhead stirrer, reflux condenser and a dropping funnel, 50 grams (0.23 mol) of tetradecane-7,8-diol (prepared above) and 60 grams (0.59 mol) triethylamine and a catalytic amount of dimethylaminopyridine (6.5 grams; 0.052 mol)) were mixed in 500 mL anhydrous hexane. The solution was cooled down with an ice bath. To this solution 97 grams (0.51 mol) decanoyl chloride was added drop-wise over a 15 minute period. Once the addition was complete, the ice bath was removed and the reaction was allowed to stir overnight. Then, an additional 12 grams of the decanoyl chloride was added and the reaction was refluxed overnight. The resulting "milky" reaction solution was neutralized with water. The resulting two layer mixture was then transferred to a separatory funnel. The organic (top) layer was separated and washed with 2×500 mL water. The aqueous layer was extracted with 3×300 mL ether. The ether extracts and the original organic layer were combined, dried over $MgSO_4$, filtered, and concentrated over a rotary evaporator at reduced pressure. The resulting residue was analyzed by NMR and infrared (IR) spectroscopies and GC/MS. Such analysis confirmed the presence of decanoic acid. The mixture was treated with 3 M aqueous solution of sodium carbonate (to neutralize the acid impurity) in 500 mL hexane. The hexane layer was dried over $MgSO_4$, filtered, and concentrated on a rotary evaporator to give the desired diester product as a colorless viscous oil with a sweet odor in 81% yield (100.5 grams). GC/MS indicated the presence of less than 1% residual acid in the product.

7. Summary

In summary, the present invention provides for methods (processes) of making diester-based lubricant compositions, wherein such methods generally comprise a step of directly diesterifying an epoxide intermediate. In some embodiments, the methods for making such diester-based lubricants utilize a biomass precursor and/or low value Fischer-Tropsch olefins and/or alcohols so as to produce high value diester-based lubricants. In some embodiments, such diester-based lubricants are derived from FT olefins and fatty acids. The fatty acids can be from a bio-based source (i.e., biomass, renewable source) or can be derived from FT alcohols via oxidation.

All patents and publications referenced herein are hereby incorporated by reference to the extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed:
1. A process comprising:
   a) epoxidizing an olefin having a carbon number of from 6 to 36 to form an epoxide having an epoxide ring, wherein the olefin is first double bond isomerized from an α-olefin to an internal olefin using an olefin isomerization catalyst; and
   b) directly esterifying the epoxide with a $C_2$ to $C_{18}$ carboxylic acid to form a diester species having viscosity and pour point suitable for use as a lubricant or component thereof.
2. The process of claim 1, wherein the step of directly esterifying is catalyzed by the presence of a catalyst.
3. The process of claim 1, wherein the catalyst is an acid catalyst selected from the group consisting of $H_3PO_4$, $H_2SO_4$, sulfonic acid, Lewis acids, silica and alumina based solid acids, amberlyst, tungsten oxide, and combinations thereof.
4. The process of claim 1, wherein the step of directly esterifying additionally comprises the presence of a carboxylic acid anhydride.
5. The process of claim 1, further comprising a Step (c) of blending the diester species with one or more other species selected from the group consisting of other diester species, Group I oils, Group II oils, Group III oils, and mixtures thereof.
6. The process of claim 1, wherein the olefin is derived from a Fischer-Tropsch process or from pyrolysis of waste plastic.
7. The process of claim 1, wherein the carboxylic acid is derived from biomass via extraction and subsequent hydrolysis of triglycerides.
8. The process of claim 1, wherein the diester species formed is selected from the group consisting of decanoic acid 2-decanoyloxy-1-hexyl-octyl ester and its isomers, tetradecanoic acid-1-hexyl-2-tetradecanoyloxy-octyl esters and its isomers, dodecanoic acid 2-dodecanoyloxy-1-hexyl-octyl ester and its isomers, hexanoic acid 2-hexanoyloxy-1-hexy-octyl ester and its isomers, octanoic acid 2-octanoyloxy-1-hexyl-octyl ester and its isomers, hexanoic acid 2-hexanoyloxy-1-pentyl-heptyl ester and isomers, octanoic acid 2-octanoyloxy-1-pentyl-heptyl ester and isomers, decanoic acid 2-decanoyloxy-1-pentyl-heptyl ester and isomers, decanoic acid-2-cecanoyloxy-1-pentyl-heptyl ester and its isomers, dodecanoic acid-2-dodecanoyloxy-1-pentyl-heptyl ester and isomers, tetradecanoic acid 1-pentyl-2-tetradecanoyloxy-heptyl ester and isomers, tetradecanoic acid 1-butyl-2-tetradecanoyloxy-hexyl ester and isomers, dodecanoic acid-1-butyl-2-dodecanoyloxy-hexyl ester and isomers, decanoic acid 1-butyl-2-decanoyloxy-hexyl ester and isomers, octanoic acid 1-butyl-2-octanoyloxy-hexyl ester and isomers, hexanoic acid 1-butyl-2-hexanoyloxy-hexyl ester and isomers, tetradecanoic acid 1-propyl-2-tetradecanoyloxy-pentyl ester and isomers, dodecanoic acid 2-dodecanoyloxy-1-propyl-pentyl ester and isomers, decanoic acid 2-decanoyloxy-1-propyl-pentyl ester and isomers, octanoic acid 2-octanoyloxy-1-propyl-pentyl ester and isomers, hexanoic acid 2-hexanoyloxy-1-propyl-pentyl ester and isomers, and mixtures thereof.
9. A process comprising:
   a) epoxidizing an olefin having a carbon number of from 6 to 36 to form an epoxide having an epoxide ring, wherein the olefin is first double bond isomerized from an α-olefin to an internal olefin in the presence of an olefin isomerization catalyst; and
   b) esterifying the epoxide with a $C_2$ to $C_{18}$ carboxylic acid, without first producing and isolating an intermediate diol species, so as to form a diester species having viscosity and pour point suitable for use as a lubricant or component thereof, wherein the step of esterifying is catalyzed by the presence of a catalyst.
10. The process of claim 9, wherein the catalyst is an acid selected from the group consisting of $H_3PO_4$, $H_2SO_4$, sulfonic acid, Lewis acids, silica and alumina-based solid acids, amberlyst, tungsten oxide, and combinations thereof.
11. The process of claim 9, wherein the step of esterifying additionally comprises the presence of a carboxylic acid anhydride.
12. The process of claim 9, wherein the olefin is derived from a Fischer-Tropsch reaction process or via pyrolysis of waste plastic.
13. The process of claim 9, wherein the carboxylic acid is derived from biomass via extraction and subsequent hydrolysis of triglycerides.
14. The process of claim 9, wherein the diester species formed is selected from the group consisting of decanoic acid 2-decanoyloxy-1-hexyl-octyl ester and its isomers, tetradecanoic acid-1-hexyl-2-tetradecanoyloxy-octyl esters and its isomers, dodecanoic acid 2-dodecanoyloxy-1-hexyl-octyl ester and its isomers, hexanoic acid 2-hexanoyloxy-1-hexy-octyl ester and its isomers, octanoic acid 2-octanoyloxy-1-hexyl-octyl ester and its isomers, hexanoic acid 2-hexanoyloxy-1-pentyl-heptyl ester and isomers, octanoic acid 2-octanoyloxy-1-pentyl-heptyl ester and isomers, decanoic acid 2-decanoyloxy-1-pentyl-heptyl ester and isomers, decanoic acid-2-cecanoyloxy-1-pentyl-heptyl ester and its isomers, dodecanoic acid-2-dodecanoyloxy-1-pentyl-heptyl ester and isomers, tetradecanoic acid 1-pentyl-2-tetradecanoyloxy-heptyl ester and isomers, tetradecanoic acid 1-butyl-2-tetradecanoyloxy-hexyl ester and isomers, dodecanoic acid-1-butyl-2-dodecanoyloxy-hexyl ester and isomers, decanoic acid 1-butyl-2-decanoyloxy-hexyl ester and isomers, octanoic acid 1-butyl-2-octanoyloxy-hexyl ester and isomers, hexanoic acid 1-butyl-2-hexanoyloxy-hexyl ester and isomers, tetradecanoic acid 1-propyl-2-tetradecanoyloxy-pentyl ester and isomers, dodecanoic acid 2-dodecanoyloxy-1-propyl-pentyl ester and isomers, decanoic acid 2-decanoyloxy-1-propyl-pentyl ester and isomers, octanoic acid 2-octanoyloxy-1-propyl-pentyl ester and isomers, hexanoic acid 2-hexanoyloxy-1-propyl-pentyl ester and isomers, and mixtures thereof.

\* \* \* \* \*